US009447027B2

(12) United States Patent
Milan et al.

(10) Patent No.: US 9,447,027 B2
(45) Date of Patent: Sep. 20, 2016

(54) TREATING LONG QT SYNDROME (75) Inventors: David J. Milan, Newton, MA (US);
David S. Peal, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 86 days.

(21) Appl. No.: 13/822,264

(22) PCT Filed: Oct. 20, 2011

(86) PCT No.: PCT/US2011/057087
§ 371 (c)(1),
(2), (4) Date: Jul. 22, 2013

(87) PCT Pub. No.: WO2012/054718
PCT Pub. Date: Apr. 26, 2012

(65) Prior Publication Data
US 2013/0310351 A1 Nov. 21, 2013

Related U.S. Application Data (60) Provisional application No. 61/405,887, filed on Oct. 22, 2010.

(51) Int. Cl.
A61K 31/165 (2006.01)
A61K 31/56 (2006.01)
C07C 235/56 (2006.01)
A61K 31/16 (2006.01)
A61K 31/166 (2006.01)
A61K 31/573 (2006.01)
A61K 31/167 (2006.01)
A61K 31/58 (2006.01)
C07C 233/75 (2006.01)

(52) U.S. Cl.
CPC ............. *C07C 235/56* (2013.01); *A61K 31/16* (2013.01); *A61K 31/166* (2013.01); *A61K 31/167* (2013.01); *A61K 31/56* (2013.01); *A61K 31/573* (2013.01); *A61K 31/58* (2013.01); *C07C 233/75* (2013.01)

(58) Field of Classification Search
USPC ........................................ 514/179, 617, 622
See application file for complete search history.

(56) References Cited

U.S. PATENT DOCUMENTS

| 4,522,811 | A  | 6/1985  | Eppstein |
| 6,468,798 | B1 | 10/2002 | Debs     |
| 6,471,996 | B1 | 10/2002 | Sokoll   |
| 6,472,375 | B1 | 10/2002 | Hoon     |

| 2004/0197271 | A1* | 10/2004 | Kunka et al. ................... 424/45 |
| 2006/0173058 | A1* | 8/2006  | Brown ................... C07C 65/05 514/381 |
| 2006/0173508 | A1* | 8/2006  | Stone ................ A61N 1/36085 607/40 |

FOREIGN PATENT DOCUMENTS

JP        11209328 A1 *  8/1999

OTHER PUBLICATIONS

Nademanee, K. et al., Annals of the New York Academy of Sciences vol. 522, pp. 536-552, published 2006.*
Chouabe, C. et al., Molecular Pharmacology vol. 54 pp. 696-703, published 1998.*
Nishizawa, S., et al., (American Journal of Emergency Medicine vol. 27, pp. 1167.e1-1167.e3, published Nov. 2009).*
Nishizawa et al., (American Journal of Emergency Medicine vol. 27, pp. 1167.e1 -1167.e3, published Nov. 2009).*
Nishizawa et al (American Journal of Emergency Medicine vol. 27, pp. 1167.e1-1167.e3, published Nov. 2009).*
Anderson et al., "Most LQT2 Mutations Reduce Kv11.1 (hERG) Current by a Class 2 (Trafficking-Deficient) Mechanism," Circulation 113:365-373, 2006, 10 pages.
Authorized officer Moon Kyoung Kim, International Search ReportNVritten Opinion in PCT/US2011/057087 mailed Apr. 10, 2012, 5 pages.
Brunner et al., "Mechanisms of cardiac arrhythmias and sudden death in transgenic rabbits with long QT syndrome," J Clin Invest. 118(6):2246-2259, 2008, 14 pages.
Hamajima et al., "Intranasal administration of HIV-DNA vaccine formulated with a polymer, carboxymethylcellulose, augments mucosal antibody production and cell-mediated immune response," Clin Immunol Immunopathol. 88 (2):205-210, 1998.
Morrow et al., "Effects of Ranolazine on Recurrent Cardiovascular Events in Patients with Non-ST-Elevation Acute Coronary Syndromes: The MERLIN-TIMI 36 Randomized Trial," JAMA 2007, 297(16):1775-1783, 12 pages.
Scirica et al., "Effect of Ranolazine, an Antianginal Agent with Novel Electrophysiological Properties, on the Incidence of Arrhythmias in Patients with Non-ST-Segment Elevation Acute Coronary Syndrome: Results from the Metabolic Efficiency With Ranolazine for Less Ischemia in Non-ST-Elevation Acute Coronary Syndrome Thrombolysis in Myocardial Infarction 36 (MERLIN-TIMI 36) Randomized Controlled Trial," Circulation 2007, 116(15);1647-52, 7 pages.
International Search Report and Written Opinion mailed Apr. 10, 2012 from international application No. PCT/US2011/057087, 5 pg.s.

* cited by examiner

*Primary Examiner* — Paul Zarek
*Assistant Examiner* — George W Kosturko
(74) *Attorney, Agent, or Firm* — Fish & Richardson P.C.

(57) ABSTRACT

This document relates to compounds useful for treating cardiac arrhythmias, for example, long QT syndrome. Also provided herein are methods and materials for using such compounds to shorten myocardial repolarization time in a patient.

25 Claims, 5 Drawing Sheets

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 1
atgcccgtgc gccgcggac                                              19

<210> SEQ ID NO 2
<211> LENGTH: 24
<212> TYPE: DNA
<213> ORGANISM: Artificial Sequence
<220> FEATURE:
```

```
<223> OTHER INFORMATION: Synthetic Oligonucleotide

<400> SEQUENCE: 2
tgcttccggg taagactgga tcgg                                              24

<210> SEQ ID NO 3
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 3
cgcgggcgga gagcatgcag cagtcctgc                                         29

<210> SEQ ID NO 4
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 4
gcaggactgc tgcatgctct ccgcccgcg                                         29
```

TREATING LONG QT SYNDROME

CLAIM OF PRIORITY

This application is a U.S. National Phase Application under 35 U.S.C. §371 of International Patent Application No. PCT/US2011/057087, filed on Oct. 20, 2011, which claims the benefit of U.S. Provisional Patent Application Ser. No. 61/405,887, filed on Oct. 22, 2010, all of which are incorporated herein by reference in their entireties.

TECHNICAL FIELD

This document relates to compounds useful for treating cardiac arrhythmias, for example, long QT syndrome (LQTS). Also provided herein are methods and materials for using such compounds to shorten myocardial repolarization time in a patient.

BACKGROUND

Long QT syndrome (LQTS) affects one in 3,000 live births and is responsible for approximately 4,000 deaths in the United States per year. The syndrome is defined clinically as an increased interval between the onset of the Q wave and the end of the T wave on the electrocardiogram, which represents a prolongation of the myocardial repolarization time. LQTS can either be congenital or acquired as a result of medication or metabolic disturbance. Many congenital forms of LQTS have been described, but the majority of cases are the result of mutations in one of three cardiac ion channel genes: KCNQ1, KCNH2, or SCN5a. Mutations in KCNQ1 or SCN5a lead to LQTS 1 and 3, while defects in KCNH2 (also known as the human ether-a-go-go related gene hERG) lead to LQTS 2.

SUMMARY

Described herein are compounds useful for treating cardiac arrhythmias, for example, LQTS. Also provided herein are methods and materials for using such compounds to shorten myocardial repolarization time in a patient. For example, a compound provided herein can be used to treat cardiac arrhythmias, such as LQTS (e.g., congenital LQTS and drug induced LQTS). In some cases, a patient is afflicted with a disease or disorder characterized by a prolonged myocardial repolarization time and can be treated with a compound provided herein (e.g., a compound of Formula (1) and/or a glucocorticoid steroid). For example, a compound of Formula (1) and/or a glucocorticoid steroid can be used to shorten myocardial repolarization time in a patient.

The methods and compositions described herein provide several advantages. For example, currently there are no therapies for the treatment of cardiac arrhythmias, such as LQTS, that address the problem of prolonged myocardial repolarization time. Current treatments include beta-blockers and implantable cardiac defibrillators (ICDs). Beta-blockers function to reduce syncope and shocks, but they are not completely reliable. Moreover, beta-blockers do not function to shorten the QT interval, but instead act only to limit the triggers. ICDs, on the other hand, do not prevent arrhythmias, but instead function to terminate arrhythmias once they have already begun. Affected patients typically receive such devices at a relatively young age, adding significantly to the burden of this disease as they will require multiple generator changes and lead revisions during their lifetime. Without wishing to be bound by theory, the compounds provided herein can not only rescue the cardiac phenotype, but can also correct the underlying cardiac repolarization defect.

Provided herein is a method for treating a cardiac arrhythmia, or for reducing risk of a cardiac arrhythmia, in a patient. In some embodiments, the method comprises administering to the patient a therapeutically effective amount of one or more compounds selected from the group consisting of:

a compound of Formula (1):

or a pharmaceutically acceptable salt form thereof,
wherein:
$R^1$ is selected from the group consisting of: hydrogen, halo, $(C_1-C_6)$alkyl, $(C_1-C_6)$haloalkyl, $-O(C_1-C_6)$alkyl, and $-C(O)R^3$;
$R^2$ is selected from the group consisting of: hydrogen, $(C_1-C_6)$alkyl, and $-O(C_1-C_6)$alkyl; and
$R^3$ is selected from the group consisting of: hydrogen and $(C_1-C_6)$alkyl; and a glucocorticoid steroid, or a pharmaceutically acceptable salt form thereof.

Also provided herein is a method for shortening myocardial repolarization time in a patient. In some embodiments, the method comprises administering to the patient a therapeutically effective amount of one or more compounds selected from the group consisting of: a compound of Formula (1) and a glucocorticoid steroid, or a pharmaceutically acceptable salt form thereof.

In the methods described above, in some embodiments, $R^2$ is a $-O(C_1-C_6)$alkyl. For example, $R^2$ can be $-O(CH_3)$.

Non-limiting examples of a compound of Formula (1) include:

or a pharmaceutically acceptable salt form thereof.
In some embodiments, the compound of Formula (1) is:

or a pharmaceutically acceptable salt form thereof.

A glucocorticoid steroid can be selected from the group consisting of: alclomethasone, amicinonide, beclomethasone, betamethasone, budesonide, carbenoxolone, ciclesonide, clobetasole, clobetasone, clocortolone, cloprednol, corticosterone, corticotropin, cortisol, cortisone, cortivazol, deflazacort, descinolone, desonide, dexamethasone, desoxymethasone, diflorasone, difluocortolone, difluprednate, flucloronide, fludrocortisone, fludroxycortide, flumethasone, flunisolide, fluocortin, fluocinonide, fluocinolone, fluocortolone, fluorometholone, fluperolone, fluprednidene, fluprednisolone, flurandrenolide, fluticasone, formocortal, halcinonide, halobetasol, halomethasone, hydrocortisone, medrysone, methylprednisolone, mometasone, nivazol, paramethasone, prednicarbate, prednisolone, prednisone, prednisolone, prednival, prednylidene, rofleponide, ticabesone, tipredane, tralonide, and triamcinolone. In some embodiments, a glucocorticoid steroid is selected from the group consisting of: dexamethasone, flurandrenolide, fluocinonide, and fluorometholone.

Cardiac arrhythmias include, for example, long QT syndrome, torsades de pointes, premature atrial contractions, wandering atrial pacemaker, multifocal atrial tachycardia, atrial flutter, atrial fibrillation, supraventricular tachycardia, AV nodal reentrant tachycardia, junctional rhythm, junctional tachycardia, premature junctional complex, premature ventricular contractions, accelerated idioventricular rhythm, monomorphic ventricular tachycardia, polymorphic ventricular tachycardia, and ventricular fibrillation. In some embodiments, the patient has long QT syndrome. For example, the patient can have long QT syndrome type 2 or drug induced long QT syndrome.

In some embodiments, one or more of the compounds provided herein may be administered acutely and/or chronically. In some embodiments, at least two of the compounds provided herein are administered to the patient. For example, in some embodiments, the administration of at least one of the two compounds is acute (e.g., a glucocorticoid steroid). In some embodiments, the administration of at least one of the two compounds is chronic (e.g., a compound of Formula (1)).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2a shows the ventricular action potential duration (APD) curves (left) of wildtype and bkd$^{-/-}$ fish treated with flurandrenolide (dashed lines). Bar graphs (right) indicate the mean APD$_{90}$ (n=7-8). FIG. 2b shows the ventricular APD curves (left) of wildtype and bkd$^{-/-}$ fish treated with 2-MMB (dashed lines). Bar graphs (right) indicate the mean APD$_{90}$ (n=7-16). (*p<0.05).

FIG. 3a summarizes the data from three Western blots indicating the amount of 155 kD (upper) cell surface isoform of zERG and zERG-I59S as a percentage of total zERG protein under various conditions. Tubulin is shown as a loading control with the asterisk indicating a p value of less than 0.05. FIG. 3b shows subcellular localization of zERG and I59S zERG compared to a surface marker. The overlay demonstrates surface expression of wildtype but not I59S zERG. Treatment with flurandrenolide or 2-MMB does not alter surface expression of I59S zERG. FIG. 3c illustrates that zERG-I59S current density is reduced compared to wildtype by providing exemplar traces from zERG (left) and zERG-I59S (middle) transfected cells. The voltage clamp protocol is provided as an inset. The current-voltage relationship for zERG (black circles) and zERG-I59S (white squares) is illustrated on the right.

FIG. 4 illustrates the results of a screen of a series of steroid compounds.

DETAILED DESCRIPTION

This document provides compounds useful for treating cardiac arrhythmias, for example, LQTS. Also provided herein are methods and materials for using such compounds to shorten myocardial repolarization time in a patient. For example, a compound provided herein can be used to treat cardiac arrhythmias, such as LQTS (e.g., congenital LQTS and drug induced LQTS). In some cases, a patient is afflicted with a disease or disorder characterized by a prolonged myocardial repolarization time and can be treated with a compound provided herein (e.g., a compound of Formula (1) and/or a glucocorticoid steroid). For example, a compound of Formula (1) and/or a glucocorticoid steroid can be used to shorten myocardial repolarization time in a patient.

Cardiac Arrhythmias

Effective, efficient ventricular pumping action depends on proper cardiac function. Proper cardiac function, in turn, relies on the synchronized contractions of the heart at regular intervals. When normal cardiac rhythm is initiated at the sinoatrial node, the heart is said to be in sinus rhythm. However, when the heart experiences irregularities in its coordinated contraction, due to electrophysiologic disturbances, e.g., caused by a disease process or from an electrical disturbance, the heart is described as being arrhythmic. The resulting cardiac arrhythmia impairs cardiac efficiency and can be a potentially life threatening event.

Cardiac arrhythmia includes any disorder where there is abnormal electrical activity in the heart. For example, cardiac arrhythmia includes LQTS, premature atrial contractions, wandering atrial pacemaker, multifocal atrial tachycardia, atrial flutter, atrial fibrillation, supraventricular tachycardia, AV nodal reentrant tachycardia, junctional rhythm, junctional tachycardia, premature junctional complex, premature ventricular contractions, accelerated idioventricular rhythm, monomorphic ventricular tachycardia, polymorphic ventricular tachycardia, and ventricular fibrillation. In some embodiments, the cardiac arrhythmia is LQTS.

LQTS is characterized by a prolongation of the myocardial repolarization time and can either be congenital or acquired as a result of medication or a metabolic disturbance (e.g., drug induced LQTS).

Congenital LQTS can arise from a mutation of one of several genes. These mutations tend to prolong the ventricular action potential duration (APD), thus lengthening the QT interval. LQTS can be inherited in an autosomal dominant or an autosomal recessive fashion. The autosomal recessive forms of LQTS tend to have a more severe phenotype, with some variants having associated syndactyly (LQT8) or congenital neural deafness (LQT1). LQTS includes, for example, LQT1, LQT2, LQT3, LQT4, LQT5, LQT6, LQT7, LQT8, LQT9, LQT10, LQT11, LQT12, LQT13, Jervell and Lange-Nielsen syndrome (JLNS), and Romano-Ward syndrome. In some embodiments, LQTS is LQT2.

Drug inducted LQTS can be triggered by any drug that triggers a prolongation of myocardial repolarization time in a patient. Such drugs include, for example, Albuterol, Alfuzosin, Amantadine, Amiodarone, Amiodarone, Amitriptyline, Amphetamine, Arsenic trioxide, Astemizole, Atazanavir, Atomoxetine, Azithromycin, Bepridil, Chloral hydrate, Chloroquine, Chlorpromazine, Ciprofloxacin, Cisapride, Citalopram, Clarithromycin, Clomipramine, Clozapine, Cocaine, Desipramine, Dexmethylphenidate, Diphenhydramine, Diphenhydramine, Disopyramide, Dobutamine, Dofetilide, Dolasetron, Domperidone, Dopamine, Doxepin, Dronedarone, Droperidol, Ephedrine, Epinephrine, Erythromycin, Escitalopram, Escitalopram, Famotidine, Felbamate, Fenfluramine, Flecainide, Fluconazole, Fluoxetine, Foscarnet, Fosphenyloin, Galantamine, Gatifloxacin, Gemifloxacin, Granisetron, Halofantrine, Haloperidol, Ibutilide, Imipramine, Indapamide, Isoproterenol, Isoproterenol, Isradipine, Itraconazole, Ketoconazole, Lapatinib, Lapatinib, Levalbuterol, Levofloxacin, Levomethadyl, Lisdexamfetamine, Lithium, Mesoridazine, Metaproterenol, Methadone, Methylphenidate, Midodrine, Moexipril/HCTZ, Moxifloxacin, Nicardipine, Nilotinib, Norepinephrine, Nortriptyline, Octreotide, Ofloxacin, Ondansetron, Oxytocin, Paliperidone, Paroxetine, Pentamidine, Perflutren lipid microspheres, Phentermine, Phenylephrine, Phenylpropanolamine, Pimozide, Probucol, Procainamide, Protriptyline, Pseudoephedrine, Quetiapine, Quinidine, Ranolazine, Risperidone, Ritodrine, Ritonavir, Roxithromycin, Salmeterol, Sertindole, Sertraline, Sibutramine, Solifenacin, Sotalol, Sparfloxacin, Sunitinib, Tacrolimus, Tamoxifen, Telithromycin, Terbutaline, Terfenadine, Thioridazine, Tizanidine, Tolterodine, Trazodone, Trimethoprim-Sulfa, Trimipramine, Vandetanib, Vardenafil, Venlafaxine, Voriconazole, Ziprasidone, and combinations thereof.

Methods of Treating Cardiac Arrhythmias

The methods provided herein include methods for the treatment of disorders associated with cardiac arrhythmias. In some embodiments, the disorder is LQTS (e.g., congenital LQTS and drug induced LQTS). Generally, the methods include administering a therapeutically effective amount of a compound (i.e., active ingredient) as described herein (i.e., a compound of Formula (1), described below, and/or a glucocorticoid steroid), to a subject who is in need of, or who has been determined to be in need of, such treatment.

As used in this context, to "treat" means to ameliorate at least one symptom of the disorder associated with cardiac arrhythmias. In some cases, cardiac arrhythmias result in prolonged myocardial repolarization time; thus, a treatment can result in the shortening of myocardial repolarization time and a return or approach to a regular cardiac rhythm. Administration of a therapeutically effective amount of a compound described herein for the treatment of a condition associated with cardiac arrhythmias will result in a shortened myocardial repolarization time.

This document provides compounds useful for treating cardiac arrhythmias, for example, long QT syndrome. In some embodiments, the cardiac arrhythmia is caused by a prolongation of myocardial repolarization time and the compounds provided herein can be used to shorten myocardial repolarization time in a patient.

Depending on the patient being treated, the compounds provided herein may be formulated and administered acutely or chronically. For example, in some embodiments, a glucocorticoid steroid is acutely administered to a patient who has a cardiac arrhythmia as described herein. In some embodiments, a compound of Formula (1) is chronically administered to a patient who has a cardiac arrhythmia as described herein.

As used herein, "acute" administration refers to administration of one or a few doses to a patient, typically at or near onset of symptoms, diagnosis of arrhythmia, or presentation for treatment, e.g., within 24 hours. In some embodiments, acute administration can be used to treat a subject who is presently experiencing arrhythmia. In some embodiments, a glucocorticoid is administered acutely.

As used herein, "chronic" administration refers to administration of more than one dose to a patient, wherein the doses are administered over a longer period of time; typically each dose is administered before the previous dose is completely cleared from the patient. In some embodiment, chronic administration can include daily administration, e.g., for a week, two weeks, a month or more, e.g., to a patient who has previously experienced arrhythmia, or is at high risk of experiencing an arrhythmia (e.g., due to personal or family history, or genetic or environmental factors; "high" risk refers to a risk above that of a normal, healthy member of the general population). Chronic administration can be used to reduce a subject's risk of experiencing a cardiac arrhythmia, e.g., in a subject who is at high risk of experiencing a cardiac arrhythmia. In some embodiments, a compound of Formula (1) as described herein is administered chronically.

In some embodiments, one or more of the compounds provided herein may be administered to a patient in the methods provided herein. For example, a glucocorticoid steroid can be administered to a patient to address an acute onset or episode of cardiac arrhythmia and a compound of Formula (1) can be administered chronically to prevent (e.g., reduce the risk of) or treat recurring cardiac arrhythmias in a patient. In some embodiments, one or more of the compounds provided herein are administered to the patient in combination. For example, one or more compounds of Formula (1) can be combined with one or more glucocorticoid steroids. The compounds can be administered together or administration of one may precede administration of the other. For example, acute administration of a glucocorticoid to treat a present arrhythmia can be followed by chronic administration of a compound of Formula (1) to treat or reduce risk of a recurrence of arrhythmia.

A compound provided herein, including a pharmaceutically acceptable salt thereof, can be purchased commercially (e.g., Prestwick and Chembridge or Sigma) or prepared using known organic synthesis techniques. For example, 2-methoxy-N-(4-methylphenyl)benzamide (2-MMB) can be prepared as follows. Briefly, o-anisoyl chloride can be added drop-wise to an equimolar quantity of p-toluidine dissolved in dichloromethane in the presence 1.1 equivalents of tri-ethylamine. The product can then be extracted against a saturated sodium bicarbonate solution and crystallized from hexane and dichloromethane to give white crystals in nearly quantitative yield.

Compounds of Formula (1)

In some embodiments, a compound provided herein can be a compound of Formula (1):

or a pharmaceutically acceptable salt form thereof, wherein:

$R^1$ is selected from the group consisting of: hydrogen, halo, $(C_1-C_6)$alkyl, $(C_1-C_6)$haloalkyl, —O$(C_1-C_6)$alkyl, and —C(O)$R^3$;

$R^2$ is selected from the group consisting of: hydrogen, $(C_1-C_6)$alkyl, and —O$(C_1-C_6)$alkyl; and

$R^3$ is selected from the group consisting of: hydrogen and $(C_1-C_6)$alkyl.

In some embodiments, $R^1$ is selected from the group consisting of hydrogen, fluoro, bromo, iodo, —$CH_3$, —$CH_2CH_3$, —$CF_3$, —$OCH_2CH_3$, and —C(O)$CH_3$. In some embodiments, $R^2$ is —O$(C_1-C_6)$alkyl. For example, $R^2$ can be —$OCH_3$ or —$OCH_2CH_3$. In some embodiments, $R^2$ is —$OCH_3$. In some embodiments, $R^3$ is hydrogen.

Non-limiting examples of a compound of Formula (1) include:

-continued or a pharmaceutically acceptable salt form thereof.

In some embodiments, the compound of Formula (1) is 2-MMB:

or a pharmaceutically acceptable salt form thereof.

Without being bound by theory, it is believed that the compounds of Formula (1) inhibit late sodium current to shorten ventricular APD (i.e. myocardial repolarization time). Accordingly, a compound of Formula (1) can function as a selective inhibitor of the late sodium current relative to peak sodium channel current, and via this mechanism, it may decrease sodium-dependent intracellular calcium overload. See, for example, (*Effect of ranolazine, an antianginal agent with novel electrophysiological properties, on the incidence of arrhythmias in patients with non ST-segment elevation acute coronary syndrome: results from the Metabolic Efficiency With Ranolazine for Less Ischemia in Non ST-Elevation Acute Coronary Syndrome Thrombolysis in Myocardial Infarction 36 (MERLIN-TIMI 36) randomized controlled trial*. Scirica B M, et al. *Circulation.* 2007; 116(15):1647-52 and *Effects of ranolazine on recurrent cardiovascular events in patients with non-ST-elevation acute coronary syndromes: the MERLIN-TIMI 36 randomized trial* Morrow D A, et al. *JAMA* 2007; 297(16):1775-83. The methods provided herein also include methods for the treatment of disorders associated with sodium-dependent intracellular calcium overload. In some embodiments, the disorder is selected from coronary artery disease and atrial fibrillation.

Glucocorticoids

In some embodiments, a compound useful in a method described herein is a glucocorticoid steroid. Glucocorticoids include a class of steroid hormones characterized by an ability to bind with the cortisol receptor. Glucocorticoid steroids are described in the *Handbook of Cancer Chemotherapy*, 6th Ed. R T Skeel; 2003 Lippincott Williams & Wilkins and the *Review of Medical Physiology*, 8th Ed., W F Ganong; 1977 Lange Medical Publications.

Non-limiting examples of glucocorticoid steroids include: alclomethasone, amicinonide, beclomethasone, betamethasone, budesonide, carbenoxolone, ciclesonide, clobetasole, clobetasone, clocortolone, cloprednol, corticosterone, corticotropin, cortisol, cortisone, cortivazol, deflazacort, descinolone, desonide, dexamethasone, desoxymethasone, diflorasone, difluocortolone, difluprednate, flucloronide, fludrocortisone, fludroxycortide, flumethasone, flunisolide, fluocortin, fluocinonide, fluocinolone, fluocortolone, fluorometholone, fluperolone, fluprednidene, fluprednisolone, flurandrenolide, fluticasone, formocortal, halcinonide, halobetasol, halomethasone, hydrocortisone, medrysone, methylprednisolone, mometasone, nivazol, paramethasone, prednicarbate, prednisolone, prednisone, prednisolone, prednival, prednylidene, rofleponide, ticabesone, tipredane, tralonide, and triamcinolone. In some embodiments, a glucocorticoid steroid is selected from the group consisting of: dexamethasone, flurandrenolide, fluocinonide, and fluorometholone.

Pharmaceutical Compositions

The methods provided herein include the manufacture and use of pharmaceutical compositions, which include compounds identified by a method provided herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

A pharmaceutical composition is typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injection can include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. The composition should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Additionally, intranasal delivery is possible, as described in, inter alia, Hamajima et al., *Clin. Immunol. Immunopathol.*, 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

The pharmaceutical compositions can be included in a container, pack, or dispenser together with instructions for administration.

DEFINITIONS

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

A "patient," as used herein, includes both humans and other animals, particularly mammals. Thus, the methods are applicable to both human therapy and veterinary applications. In some embodiments, the patient is a mammal, for example, a primate. In some embodiments, the patient is a human.

A "therapeutically effective" amount of a compound provided herein is typically one which is sufficient to achieve the desired effect and may vary according to the nature and severity of the disease condition, and the potency of the compound. It will be appreciated that different concentrations may be employed for prophylaxis than for treatment of an active disease.

The term, "compound," as used herein is meant to include all stereoisomers, geometric isomers, and tautomers of the structures depicted. Compounds herein identified by name or structure as one particular tautomeric form are intended to include other tautomeric forms unless otherwise specified.

In some embodiments, a compound provided herein, or salt thereof, is substantially isolated. By "substantially isolated" is meant that the compound is at least partially or substantially separated from the environment in which it was formed or detected. Partial separation can include, for example, a composition enriched in the compound provided herein. Substantial separation can include compositions containing at least about 50%, at least about 60%, at least about 70%, at least about 80%, at least about 90%, at least about 95%, at least about 97%, or at least about 99% by weight of the compound provided herein, or salt thereof. Methods for isolating compounds and their salts are routine in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "alkyl" includes straight-chain alkyl groups (e.g., methyl, ethyl, propyl, butyl, pentyl, hexyl, heptyl, octyl, nonyl, and decyl) and branched-chain alkyl groups (isopropyl, tert-butyl, isobutyl, and sec-butyl), cycloalkyl (alicyclic) groups (cyclopropyl, cyclopentyl, cyclohexyl, cycloheptyl, and cyclooctyl), alkyl substituted cycloalkyl groups, and cycloalkyl substituted alkyl groups. In certain embodiments, a straight chain or branched chain alkyl has six or fewer carbon atoms in its backbone (e.g., $C_1$-$C_6$ for straight chain; $C_3$-$C_6$ for branched chain). The term $C_1$-$C_6$ includes alkyl groups containing 1 to 6 carbon atoms.

The term "halo" includes chloro, bromo, iodo, and fluoro.

EXAMPLES

The invention is further described in the following examples, which do not limit the scope of the invention described in the claims.

Example 1

Compound Screen 1200 small-molecule compounds from a commercially available small molecule library were screened for the ability to rescue zebrafish LQT2 breakdance embryos to identify compounds that shorten ventricular action potential durations (APDs). The zebrafish breakdance (bkd) mutant carries an I59S mutation in KCNH2, the LQTS 2 gene, and has an easily observed cardiac phenotype. Moreover, the I59S KCNH2 mutation faithfully recapitulates in the zebrafish embryos many features of human LQTS: ventricular APD prolongation, spontaneous early after depolarizations, and 2:1 atrioventricular conduction (AV) block in early stages of development. Since cell-based chemical screens for trafficking rescue are susceptible to high false positive rates due to the presence of KCNH2 inhibitors in many chemical libraries, and because they focus on a single mechanism of rescue, the hypothesis that the zebrafish LQTS 2 model breakdance could provide a functional phenotypic screen for compounds that shorten myocardial repolarization was tested.

Breakdance homozygotes (bkd$^{-/-}$) develop 2:1 atrioventricular conduction block (two atrial beats for each ventricular beat) that is the result of a prolonged refractory period in the ventricle. This phenotype can be scored in vivo, owing to the transparency of the embryo, enabling a straightforward small molecule suppressor screen. Breakdance homozygotes are viable and fertile, with phenotypic penetrance of 92-96%.

Tubingen AB (TuAB) and tb218 (bkd$^{-/-}$) fish were maintained using standard methods. For screening, tb218$^{-/-}$ adults were crossed, and embryos were reared in E3 buffer at 25° C. 24 hours post-fertilization (hpf) animals were dechorionated with proteinase-K. In order to minimize false positive results, three bkd$^{-/-}$ embryos were plated in each well and compounds were only scored as a hit if all three embryos were rescued. Accordingly, dechorionated embryos were plated three per well in 96-well plates in a final volume of 200 μL. At 48 hpf, library compounds (Prestwick and Chembridge) were added to a final concentration of 10 ng/μL. Zebrafish were visually scored at 72 hpf for presence or absence of a 2:1 AV block. The embryos were tested after the onset of atrioventricular block in order to identify compounds that could specifically treat LQTS rather than compounds that exert their effects primarily by altering cardiac development.

Figure 1:
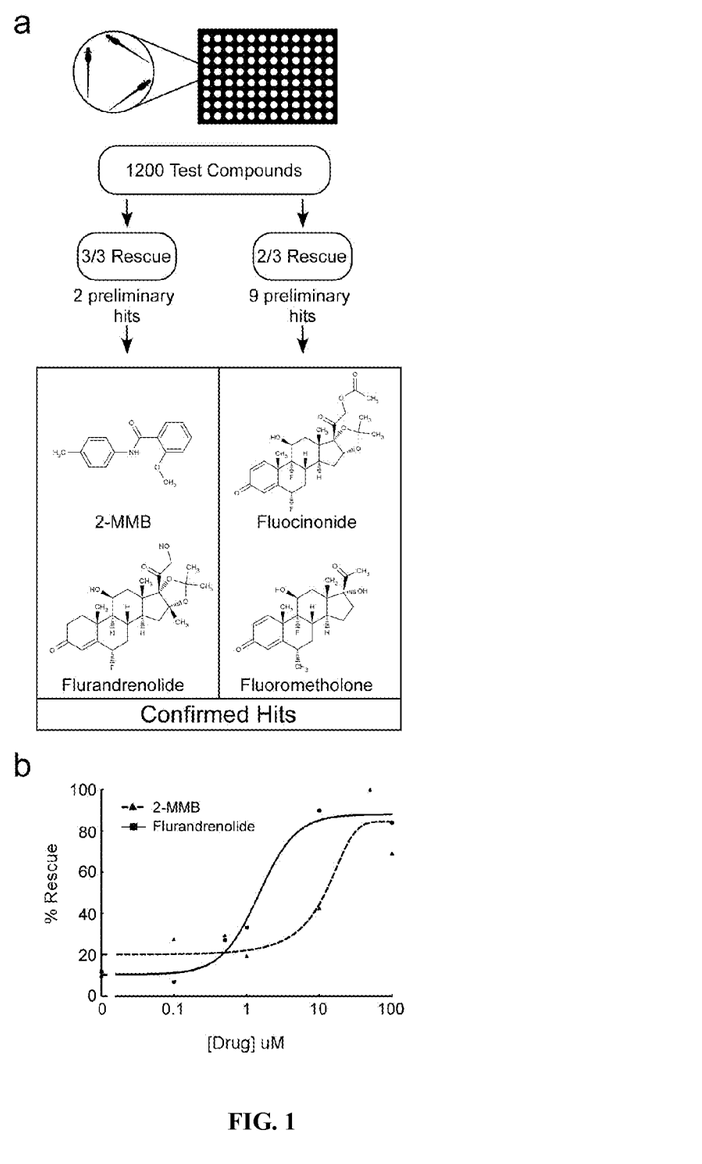
FIG. 1a is a flow chart illustrating the small molecule screening strategy and lead compounds.
FIG. 1b a line drawing illustrating the dose-response curve of two of the lead compounds, 2-MMB and flurandrenolide.

In a screen of 1,200 chemicals, two compounds were identified that ameliorated the 2:1 AV block, the long QT phenotype, in all three embryos, 2-methoxy-N-(4-methylphenyl)benzamide (2-MMB) and the steroid flurandrenolide (FIG. 1a). Nine compounds rescued two of three embryos in the well. Two of these confirmed on follow-up and were found to be the steroids, fluocinonide and fluorometholone (FIG. 1a).

For dose response curves, tb218 fish at 48 hpf were treated for 24 hours with 2-MMB or flurandrenolide (Sigma) from 0.1 M stock solutions in DMSO to a final concentration of 10 μM for flurandrenolide and 50 μM for 2-MMB. The wells were then scored for suppression of the breakdance phenotype at indicated times.

Flurandrenolide and 2-MMB displayed dose related suppression of the breakdance phenotype with $ED_{50s}$ of approximately 2 μM and 10 μM respectively (FIG. 1b). Time series experiments revealed higher rescue at later time points for both flurandrenolide and 2-MMB, but a slightly longer exposure requirement for flurandrenolide. Time course experiments and structure activity analyses are consistent with the hypothesis that 2-MMB inhibits late sodium current to shorten ventricular APDs. In contrast, rescue with flurandrenolide was abrogated by knockdown of the glucocorticoid receptor, but not the androgen receptor, suggesting it acts at a transcriptional level via the glucocorticoid receptor to shorten APDs.

Example 2

Optical Mapping

In order to directly measure the effects of these compounds on myocardial repolarization, ventricular action potential durations were measured using voltage sensitive optical mapping in bkd$^{-/-}$ and wildtype fish treated with active compounds or diluent. Optical voltage mapping of embryonic hearts was performed as described previously (see Brunner, M. et al. *J Clin Invest* 118, 2246-59 (2008)). Mapping was performed on tb218 or TuAB hearts from embryos that had been treated with 100 μM of 2-MMB and flurandrenolide starting at 48 hpf. Explanted hearts were mapped at 72-75 hpf for 2-MMB treatment, and at 96-99 hpf for flurandrenolide treatment. Control fish for each time point were treated with 0.1% DMSO.

Figure 2:
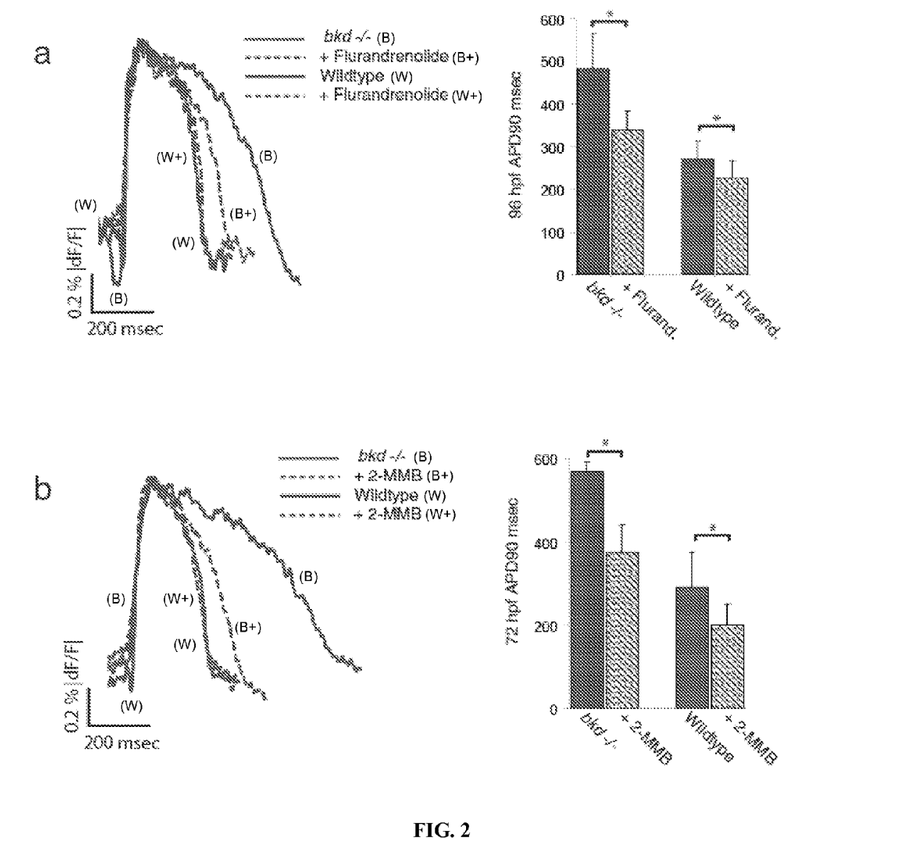
FIG. 2 illustrates that treatment of the breakdance mutant with flurandrenolide and 2-MMB partially corrects a repolarization defect.

Treatment of bkd$^{-/-}$ embryos with 50 μM flurandrenolide at 48 hpf and recording at 96 hpf revealed drug-mediated shortening of ventricular action potential durations from 482+/−83 msec to 338+/−44 msec (p<0.05, FIG. 2a) and a smaller but statistically significant effect on wildtype fish shortening action potentials from 271+/−43 msec to 227+/−41 msec (p<0.05, FIG. 2a). Treatment with 50 μM 2-MMB at 48 hpf and recording at 72 hpf resulted in drug-mediated shortening of ventricular action potential durations in bkd$^{-/-}$ embryos from 570+/−23 msec to 376+/−66 msec, (p<0.05, FIG. 2b), and had smaller, but significant effect in wildtype embryos with controls displaying APD90 of 290+/−85 msec versus 200+/−51 ms with 2-MMB, (p<0.05, FIG. 2b). Both lead compounds achieved suppression of the long QT phenotype by shortening repolarization time.

Example 3

Characterization of the bkd I59S Mutation

In order to better understand the mechanisms of compounds 2-MMB and flurandrenolide in breakdance embryos, the nature of the bkd I59S mutation was characterized.

Zebrafish zERG in a pSport vector was acquired from Open Biosystems (accession number AF532865). PCR amplification (Forward:atgcccgtgcgccgcggac (SEQ ID NO:1), Reverse:tgcttccgggtaagactggatcgg (SEQ ID NO:2))

and subcloning into pcDNA3.2/V5/GW/D-TOPO (Invitrogen, #K2440-20) resulted in the sequence verified clone zERG-V5. Site-directed mutagenesis (QuikChange II, Stratagene, #200523-12) using F1-cgcgggcggagaGcatgcagcagtcctgc (SEQ ID NO:3), R1-gcaggactgctgcatgCtctccgcccgcg (SEQ ID NO:4) resulted in zERG-V5 I59S.

HEK293 (ATCC, #CRL-1573) and COS7 (ATCC, #CRL-1651) cells were maintained in Dulbeco modified Eagle medium (DMEM) with 10% FBS, 1% Glutamine and 1% Pen-Strep. Cells were transfected using Lipofectamine LTX Reagent (Invitrogen, #15338) according to the manufacturer's instructions. For immunofluorescence, transfected cells were rinsed with ice-cold PBS and treated with 2.5 µg/mL of FITC-labeled wheat germ agglutinin (WGA, Sigma, #L4895) for three minutes on ice. Cells were rinsed with PBS, fixed in 4% paraformaldehyde, and permeabilized with 0.2% Triton X-100. Standard immunofluorescence using a murine anti-V5 antibody (Invitrogen, #46-1157, 1:5000), and an Alexafluor 555 conjugated secondary (Invitrogen, #A21424, 1:5000) was performed and cells were imaged using a Zeiss LSM 5 Pascal confocal microscope. Transfected HEK293 cells were treated with 2-MMB or flurandrenolide from DMSO stock solutions to 1004 for 24 hours for Western Blots and immunofluorescence. Western blots were performed using standard techniques with the mouse anti-V5 primary described above (1:5000) and an HRP conjugated secondary antibody (Thermo Scientific #31444 at 1:5000) for V5 epitope detection. Tubulin controls were measured with mouse anti-tubulin antibody (Millipore, #05-829, 1:5000) and the same secondary. Blots were visualized using a chemiluminescent substrate (Pierce, #32106) and subsequent film exposure.

Figure 3:
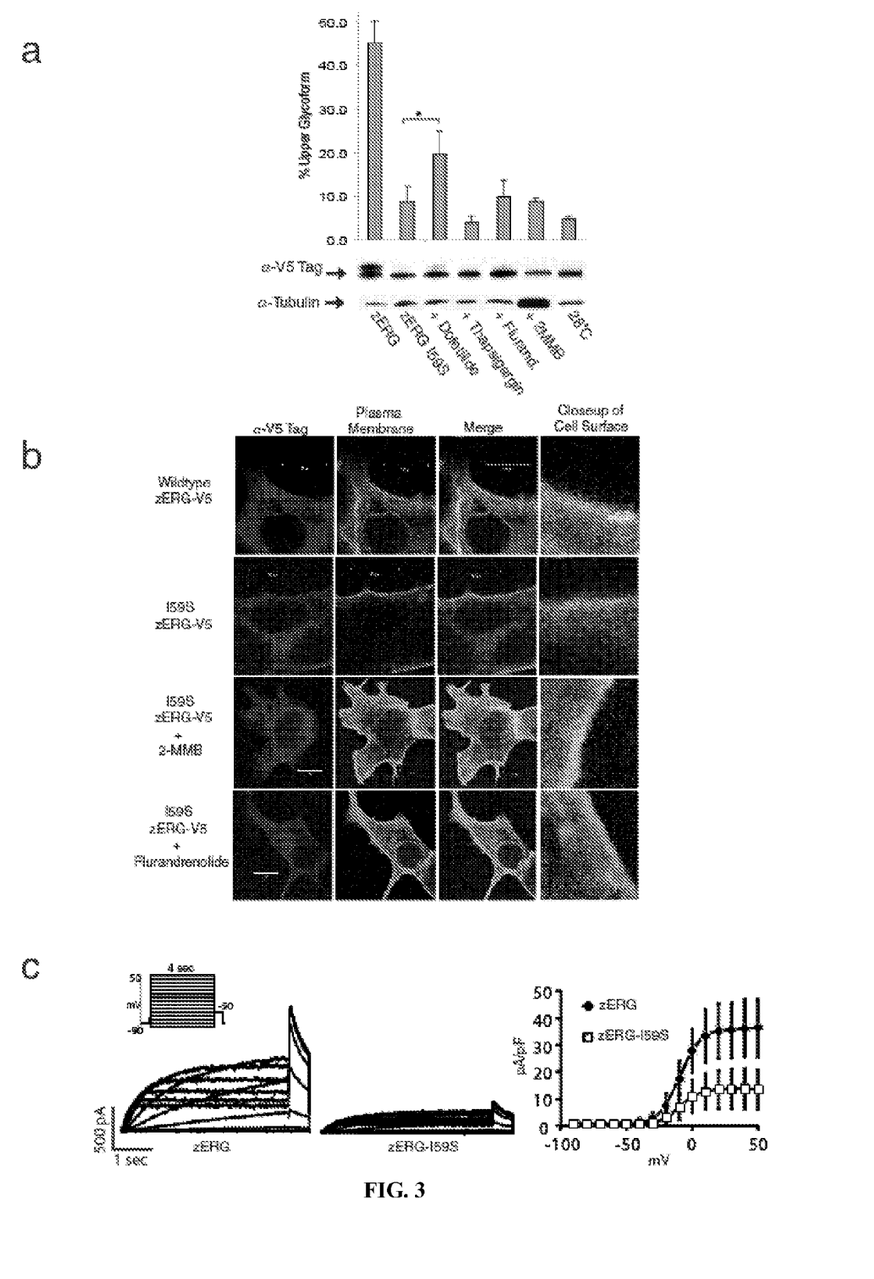
FIG. 3 shows a zERG I59S mutation leading to a trafficking defect that is not corrected by flurandrenolide or 2-MMB.

Transfection of a C-terminal V5 epitope tagged zebrafish ERG (zERG) in HEK cells produced a protein that runs as a doublet at 133 kD and 155 kD (FIG. 3a). This pattern is similar to the human KCNH2 protein where it has been established that the lower band is the core glycosylated protein while the upper band is a mature glycoform that traffics to the membrane. In the majority of human KCNH2 mutations studied to date the mature glycoform fails to develop and the protein does not traffic appropriately to the cell membrane. Expression of I59S zERG in HEK cells resulted in a protein that runs at 133 kD on Western blot, with only a faint upper glycoform at 155 kD (FIG. 3a), which represents an 83% reduction in the cell surface isoform. Immunofluorescence of the wild type zERG-V5 in HEK cells revealed colocalization with a cell surface marker (see FIG. 3b), while I59S zERG-V5 did not colocalize with the surface marker. These data demonstrate that, similar to the majority of known human mutations, the I59S zERG mutation results in a trafficking defect.

Example 4

Patch Clamp Electrophysiology

To further characterize the I59S zERG mutation, patch clamp electrophysiology was performed on HEK cells transfected with either wildtype zERG or I59S zERG.

Whole-cell currents were recorded using the disrupted patch technique in COST cells transiently expressing wild-type or I59S zERG. Recordings were performed at room temperature 48 hours after transfection. The bath solution contained (in mM) 150 NaCl, 5.4 KCl, 1.8 $CaCl_2$, 1 MgCl, and 5 HEPES (pH adjusted to 7.4 with NaOH). Fire-polished patch electrodes had 2-5MΩ tip resistance when filled with (in mM) 150 KCl, 5 $Mg_2ATP_3$, 2 MgCl, 5 BAPTA, and 10 HEPES (pH adjusted to 7.2 with KOH). Recordings were low-pass filtered at 5 kHz with an Axopatch 200B amplifier and digitized at 10 kHz with a Digidata 1322 A A/D converter, both controlled using Clampex software, and later analyzed using Clampfit software (Axon Instruments, CA). Capacitive transients were electronically subtracted, and cell capacitance noted. Cells were clamped at a holding potential of −80 mV, sequentially stepped to test potentials ranging from −90 and +50 mV for four seconds, followed by a step to −50 mV for 500 milliseconds to elicit typical zERG tail currents. Current density-voltage relations were derived from peak tail current values divided by cell capacitance, and were fit to a standard Boltzmann function. Boltzmann-fit maxima were compared by Student's t-test with $p<0.05$ considered significant.

Although both the wildtype and mutant give rise to an outward potassium current, there was a marked reduction in maximal current density in the I59S zERG mutant compared to the wildtype zERG (13+/−7 pA/pF versus 36+/−10 pA/pF, $p<0.05$, FIG. 3c). The current voltage relationship for the tail current was not otherwise appreciably different between wildtype and I59S mutant channels.

Several distinct manipulations have been shown to correct the trafficking defect of various subsets of mutant hERG proteins, including incubation at lower temperature, treatment with $I_{Kr}$ blocking drugs, and treatment with thapsigargin (see Anderson, C. L. et al. Circulation 113, 365-73 (2006)). The upper protein band of the zERG mutant I59S was partially restored by incubation with dofetilide, a potent KCNH2 inhibitor, but not by growth at low temperature, or treatment with thapsigargin (FIG. 3a). These experiments demonstrate that, similar to many of the human trafficking defective mutant KCNH2 proteins, the bkd trafficking defect can be partially corrected by KCNH2 inhibitors.

Example 5

Suppression of the bkd Phenotype by Identified Compounds

In order to determine how 2-MMB and flurandrenolide act to suppress the bkd phenotype, it was determined whether treatment with 2-MMB or flurandrenolide would correct I59S zERG trafficking Treatment of HEK cells transfected with I59S zERG with 100 µM 2-MMB or flurandrenolide for 24 hours did not appreciably change the percentage of the mature glycoform on Western blot (FIG. 3a) or affect the membrane localization measured by immunofluorescence (FIG. 3b). In addition, neither flurandrenolide nor 2-MMB was able to rescue the defective trafficking of the human KCNH2 G601S mutant. These data suggest that 2-MMB and flurandrenolide do not suppress the breakdance phenotype by correcting defective I59S zERG trafficking, and confirm the utility of this physiologic screen in identifying chemical suppressors that function via alternative mechanisms to trafficking rescue.

Example 6

Steroid Compound Screen

For the dose response curves, Zebrafish harboring the I59S KCNH2 mutation (breakdance) were treated with dexamethasone, flurandrenolide, testosterone, and deoxycorticosterone acetate at doses of 0.1, 0.5, 1, 10, 50 and 100 µM for 24 hours prior to assessment of percentage rescue from 2:1 AV block (24 fish per sample).

Figure 4A:
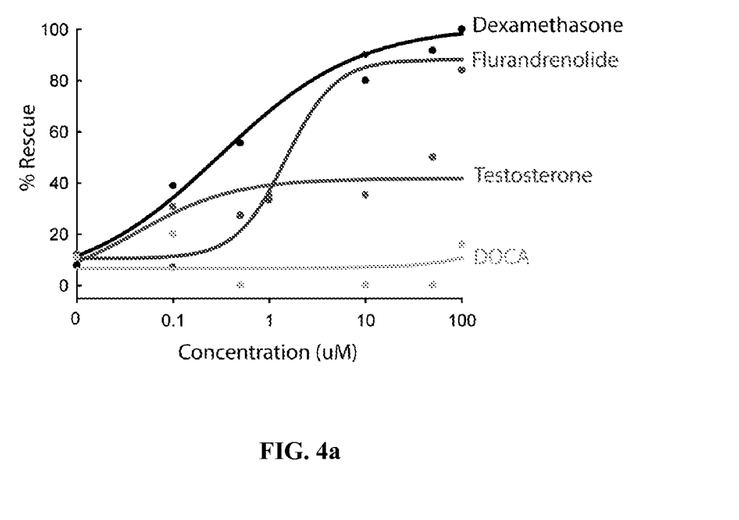
FIG. 4a compares the dose-response curve of four steroids known to act through specific signaling pathways: dexamethasone (glucocorticoid pathway), testosterone (androgen pathway), and DOCA (mineralcorticoid pathway).
Figure 4B:
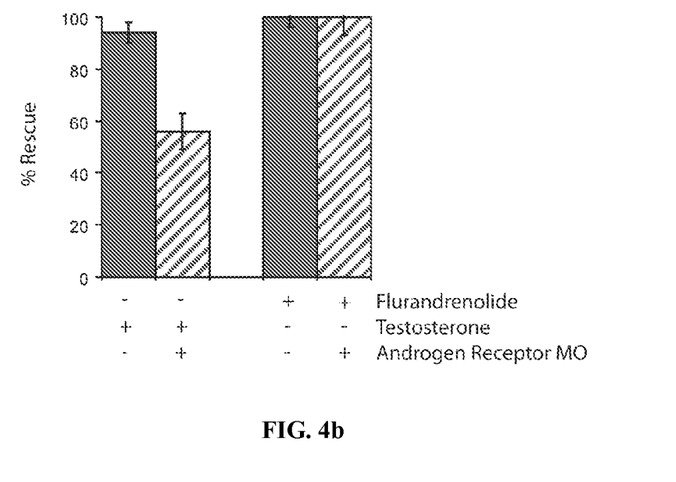
FIG. 4b is a bar graph illustrating that the knockdown of the glucocorticoid receptor blocks rescue of LQT by flurandrenolide and dexamethasone (n=26 to 31).
Figure 4C:
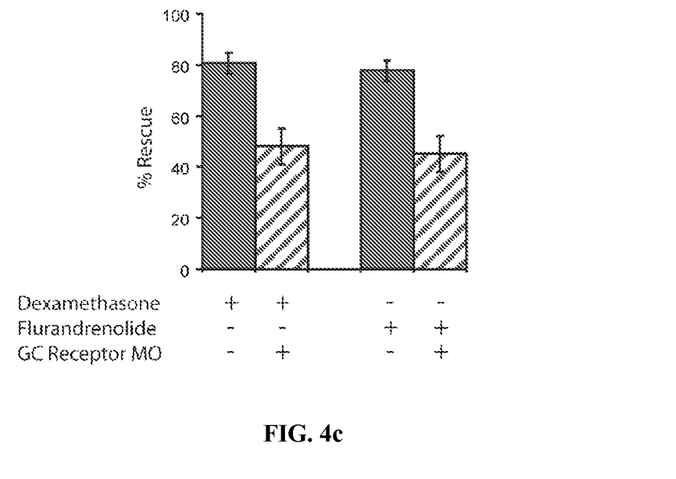
FIG. 4c is a bar graph illustrating that androgen receptor knockdown does not affect rescue of bkd–/– by glucocorticoids.

As shown in FIG. 4a, the results demonstrate rescue by dexamethasone and flurandrenolide, weaker rescue by testosterone, and no activity of the pure mineralocorticoid deoxycorticosterone acetate (DOCA). FIGS. 4b and 4c illustrate that the knockdown of the glucocorticoid receptor blocks rescue of LQT by flurandrenolide and dexamethasone (n=26 to 31), while androgen receptor knockdown does not affect rescue of bkd−/− by glucocorticoids.

Example 7

Structure Activity Relationship for Derivatives of 2-MMB

Zebrafish harboring the I59S mutation were treated with 2-MMB, and 17 structural orthologs (see Table 1 below), at 10 μM for 48 hours prior to assessment of the percent of fish rescued from 2:1 AV block. Results demonstrate activity in several of the structural orthologs.

TABLE 1

| $R^1$ | $R^2$ | Rescue (%) |
|---|---|---|
| —4-CH$_3$ | —2-OCH$_3$ | 67 |
| —H | —2-OCH$_3$ | 7 |
| —4-CH$_2$CH$_3$ | —2-OCH$_3$ | 53 |
| —4-CF$_3$ | —2-OCH$_3$ | 33 |
| —4-sec-butyl | —2-OCH$_3$ | 0 |
| —4-F | —2-OCH$_3$ | 66 |
| —4-Br | —2-OCH$_3$ | 7 |
| —4-I | —2-OCH$_3$ | 64 |
| —4-C(O)CH$_3$ | —2-OCH$_3$ | 20 |
| —3-CH$_3$ | —2-O—CH$_2$CH$_3$ | 3 |
| —4-O—CH$_2$CH$_3$ | —2-O—CH$_2$CH$_3$ | 50 |
| —4-F | —2-O—CH$_2$CH$_3$ | 3 |
| —2-CH$_3$ | —2-O—CH$_2$CH$_3$ | 0 |
| —3-OCH$_3$ | —2-OCH$_3$ | 3 |
| —4-O—CH$_2$CH$_3$ | —2-OCH$_3$ | 0 |
| —4-OCH$_3$ | —2-OCH$_3$ | 0 |
| —H | —2-OCH$_3$, —3-CH$_3$ | 0 |

Example 8

Rabbit Pharmacokinetic Studies

For rabbit pharmacokinetic studies, 10 mg of 2-MMB diluted in phosphate buffered saline was injected over 30 seconds. Blood samples were obtained at 15 seconds, 30 seconds, 45 seconds, 1 minute, 90 seconds, 2 minutes, 3 minutes, 4 minutes, minutes, 7.5 minutes, and 10 minutes. Samples were extracted and 2-MMB was quantified as a function of time. Data points were fit to an exponential decay with single time constant which revealed an estimated serum half-life of 15 seconds.

Example 9

Cellular Mechanistic Experiments

For cellular mechanistic experiments, wild type and I59S KCNH2 mutant zebrafish hearts were dissected using standard techniques, the hearts were treated with collagenase I and protease XIV in Hank's Buffer for 15-30 minutes and then plated on polylysine coated coverslips. Whole cell patch clamp recordings (as in Example 4) from individual cells and cell-clusters were obtained in current-clamp mode both at baseline and after perfusion with 10 μM 2-MMB solution.

Whole cell current clamp recordings from wild type and I59S KCNH2 mutants confirmed longer action potential durations in the mutant cells compared to wild type. Further, application of 2-MMB to mutant cardiomyocytes resulted in shortening of the action potential confirming the drug's effect. The technology will enable the isolation of individual current in voltage clamp mode in order to determine the mechanism of 2-MMB.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating long QT syndrome in a patient in need thereof, the method comprising administering to the patient a therapeutically effective amount of one or more compounds of Formula (1):

or a pharmaceutically acceptable salt form thereof, wherein:

$R^1$ is selected from the group consisting of: hydrogen, halo, $(C_1-C_6)$alkyl, $(C_1-C_6)$haloalkyl, $-O(C_1-C_6)$alkyl, and $-C(O)R^3$;

$R^2$ is selected from the group consisting of: hydrogen, $(C_1-C_6)$alkyl, and $-O(C_1-C_6)$alkyl; and

$R^3$ is selected from the group consisting of: hydrogen and $(C_1-C_6)$alkyl; or a pharmaceutically acceptable salt form thereof.

2. The method of claim 1, wherein administration of the compound of Formula (I) shortens the myocardial repolarization time in the patient.

3. The method of claim 1, wherein $R^2$ is a $-O(C_1-C_6)$alkyl.

4. The method of claim 3, wherein $R^2$ is $-O(CH_3)$.

5. The method of claim 1, wherein the compound of Formula (1) is selected from the group consisting of:

-continued or a pharmaceutically acceptable salt form thereof.

6. The method of claim 5, wherein the compound of Formula (1) is:

or a pharmaceutically acceptable salt form thereof.

7. The method of claim 1, wherein the patient has long QT syndrome type 2.

8. The method of claim 1, wherein the long QT syndrome is drug induced long QT syndrome.

9. The method of claim 1, wherein the administration of the one or more compounds of Formula (1) is acute.

10. The method of claim 1, wherein the administration of the one or more compounds of Formula (1) is chronic.

11. The method of claim 1, wherein at least two compounds are administered to the patient.

12. The method of claim 11, wherein the administration of at least one of the two compounds is acute.

13. The method of claim 11, wherein the administration of at least one of the two compounds is chronic.

14. The method of claim 1, wherein the method further comprises administering one or more glucocorticoid steroids, or a pharmaceutically acceptable salt form thereof.

15. The method of claim 14, wherein the glucocorticoid steroid is selected from the group consisting of: alclomethasone, amicinonide, beclomethasone, betamethasone, budesonide, carbenoxolone, ciclesonide, clobetasole, clobetasone, clocortolone, cloprednol, corticosterone, corticotropin, cortisol, cortisone, cortivazol, deflazacort, descinolone, desonide, dexamethasone, desoxymethasone, diflorasone, difluocortolone, difluprednate, flucloronide, fludrocortisone, fludroxycortide, flumethasone, flunisolide, fluocortin, fluocinonide, fluocinolone, fluocortolone, fluorometholone, fluperolone, fluprednidene, fluprednisolone, flurandrenolide, fluticasone, formocortal, halcinonide, halobetasol, halomethasone, hydrocortisone, medrysone, methylprednisolone, mometasone, nivazol, paramethasone, prednicarbate, prednisolone, prednisone, prednival, prednylidene, rofleponide, ticabesone, tipredane, tralonide, and triamcinolone.

16. The method of claim 15, wherein the glucocorticoid steroid is selected from the group consisting of: dexamethasone, flurandrenolide, fluocinonide, and fluorometholone.

17. A method for treating long QT syndrome in a patient in need thereof, the method comprising administering to the patient a therapeutically effective amount of one or more glucocorticoid steroids, or a pharmaceutically acceptable salt form thereof.

18. The method of claim 17, wherein the patient has long QT syndrome type 2.

19. The method of claim 17, wherein the long QT syndrome is drug induced long QT syndrome.

20. The method of claim 17, wherein the administration of the one or more glucocorticoid steroids is acute.

21. The method of claim 17, wherein the administration of the one or more glucocorticoid steroids is chronic.

22. The method of claim 17, wherein the glucocorticoid steroid is selected from the group consisting of: alclomethasone, amicinonide, beclomethasone, betamethasone, budesonide carbenoxolone, ciclesonide, clobetasole, clobetasone, clocortolone, cloprednol, corticosterone, corticotropin, cortisol, cortisone, cortivazol, deflazacort, descinolone, desonide, dexamethasone, desoxymethasone, diflorasone, difluocortolone, difluprednate, flucloronide, fludrocortisone, fludroxycortide, flumethasone, flunisolide, fluocortin, fluocinonide, fluocinolone, fluocortolone, fluorometholone, fluperolone, fluprednidene, fluprednisolone, flurandrenolide, fluticasone, formocortal, halcinonide, halobetasol, halomethasone, hydrocortisone, medrysone, methylprednisolone, mometasone, nivazol, paramethasone, prednicarbate, prednisolone, prednisone, prednival, prednylidene, rofleponide, ticabesone, tipredane, tralonide, and triamcinolone.

23. The method of claim 22, wherein the glucocorticoid steroid is selected from the group consisting of: dexamethasone, flurandrenolide, fluocinonide, and fluorometholone.

24. The method of claim 14, wherein the method comprises acute administration of the one or more glucocorticoid steroids, or a pharmaceutically acceptable salt form thereof.

25. The method of claim 14, wherein the method comprises chronic administration of the compound of Formula (1), or a pharmaceutically acceptable salt form thereof.

* * * * *

UNITED STATES PATENT AND TRADEMARK OFFICE
CERTIFICATE OF CORRECTION

PATENT NO. : 9,447,027 B2  
APPLICATION NO. : 13/822264  
DATED : September 20, 2016  
INVENTOR(S) : David J. Milan et al.

Page 1 of 1

It is certified that error appears in the above-identified patent and that said Letters Patent is hereby corrected as shown below:

On the Title Page

In Column 2 (Other Publications), Line 15, delete "ReportNVritten" and insert -- Report/Written --, In the Claims In Column 21, Line 60, in Claim 2, delete "(I)" and insert -- (1) --, In Column 24, Line 20, in Claim 15, delete "amicinonide," and insert -- amcinonide, --, In Column 24, Line 21, in Claim 15, delete "clobetasole," and insert -- clobetasol, --, In Column 24, Line 30, in Claim 15, delete "halomethasone," and insert -- halometasone, --, In Column 24, Line 31, in Claim 15, delete "momethasone," and insert -- mometasone, --, In Column 24, Line 53, in Claim 22, delete "amicinonide," and insert -- amcinonide, --,

In Column 24, Lines 53-54, in Claim 22, after "budesonide" insert -- , --, In Column 24, Line 54, in Claim 22, delete "clobetasole," and insert -- clobetasol, --, In Column 24, Line 63, in Claim 22, delete "halomethasone," and insert -- halometasone, --, In Column 24, Line 64, in Claim 22, delete "momethasone," and insert -- mometasone, --.

Signed and Sealed this  
Eleventh Day of April, 2017

Michelle K. Lee  
*Director of the United States Patent and Trademark Office*